(12) United States Patent
Kaski

(10) Patent No.: US 7,460,902 B2
(45) Date of Patent: Dec. 2, 2008

(54) MONITORING OF ATRIAL ACTIVATION

(75) Inventor: Mikko Kaski, Espoo (FI)

(73) Assignee: The General Electric Company, Schenectady, NY (US)

( * ) Notice: Subject to any disclaimer, the term of this patent is extended or adjusted under 35 U.S.C. 154(b) by 216 days.

(21) Appl. No.: 11/049,548

(22) Filed: Feb. 2, 2005

(65) Prior Publication Data

US 2006/0173369 A1    Aug. 3, 2006

(51) Int. Cl.
*A61B 5/04* (2006.01)
*A61B 5/0452* (2006.01)
*A61B 5/0472* (2006.01)

(52) U.S. Cl. .................... 600/513; 600/509; 600/516

(58) Field of Classification Search ......... 600/508–509, 600/515–516, 518, 513, 517
See application file for complete search history.

(56) References Cited

U.S. PATENT DOCUMENTS

| | | | |
|---|---|---|---|
| 4,510,944 A * | 4/1985 | Porges | 600/500 |
| 4,510,945 A * | 4/1985 | Barreras | 600/509 |
| 4,569,350 A * | 2/1986 | Mumford et al. | 600/510 |
| 6,389,316 B1 * | 5/2002 | Bornzin et al. | 607/28 |
| 6,480,741 B1 * | 11/2002 | Morris | 607/27 |
| 6,718,206 B2 * | 4/2004 | Casavant | 607/9 |
| 7,136,694 B2 * | 11/2006 | Hadley et al. | 600/515 |
| 2002/0091330 A1 * | 7/2002 | MacAdam et al. | 600/509 |
| 2005/0215914 A1 * | 9/2005 | Bornzin et al. | 600/508 |

OTHER PUBLICATIONS

"The Principles of Software QRS Detection", Kohler, B.-U.; Hennig, C;. Orglmeister, R.; Engineering in Medicine and Biology Magazine, IEEE, Jan.-Feb. 2002, vol. 21, Issue 1, pp. 42-57.

* cited by examiner

*Primary Examiner*—Carl H Layno
*Assistant Examiner*—Natasha N Patel
(74) *Attorney, Agent, or Firm*—Andrus, Sceales, Starke & Sawall, LLP

(57) ABSTRACT

A method and system for monitoring atrial activation in a patient is provided. In the method, a moment of occurrence and a wave form are predicted for a subsequent P wave based on a sequence of P waves already received in ECG signal data obtained from the patient. The process then checks whether the subsequent P wave really occurs in the ECG signal data within a first time window around the predicted moment of occurrence. If this is the case, the process further monitors whether the P wave is followed by a QRS complex in the ECG signal data.

24 Claims, 7 Drawing Sheets

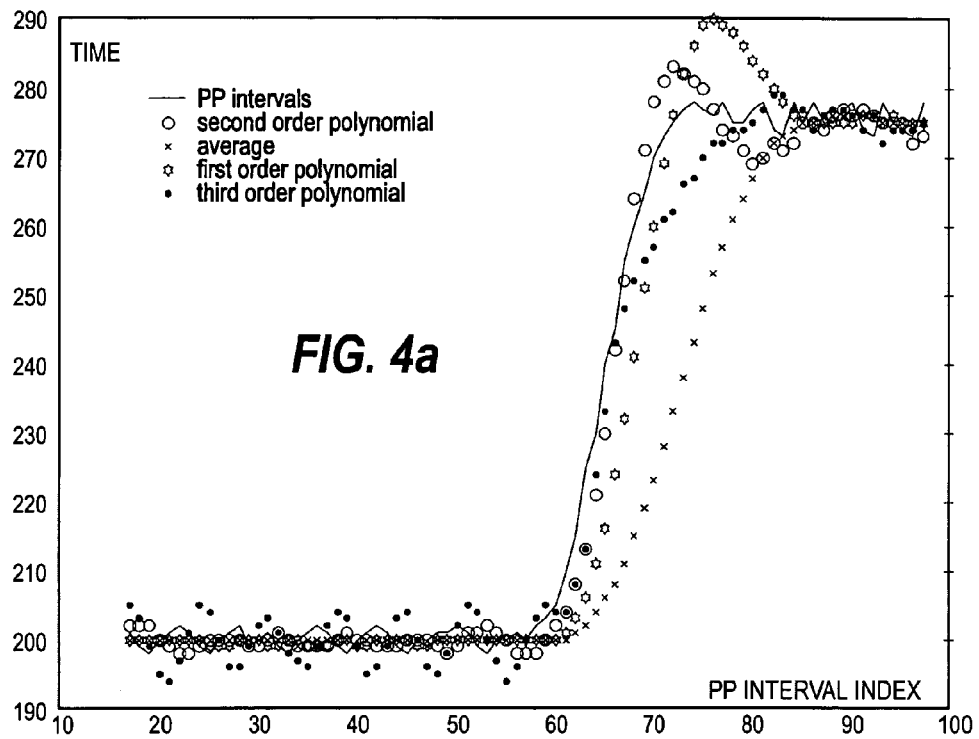
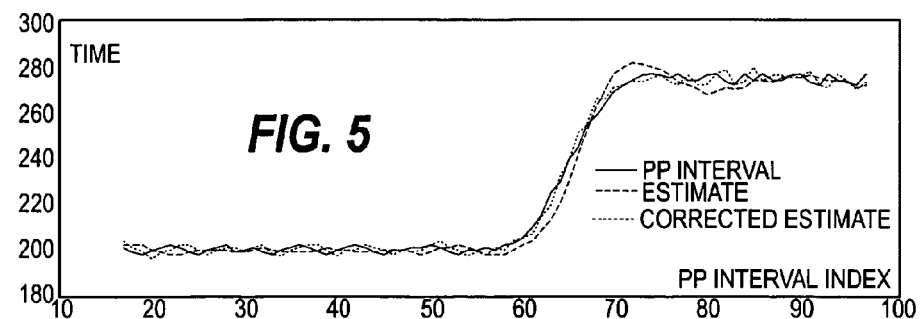
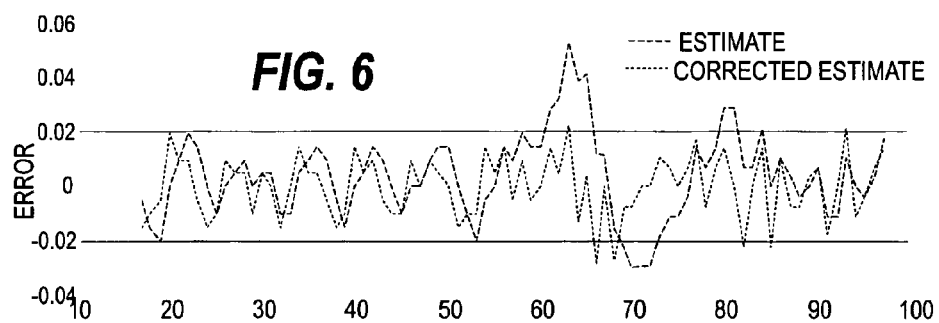

MONITORING OF ATRIAL ACTIVATION

FIELD OF THE INVENTION

The present invention relates generally to the monitoring of atrial activation, especially to the detection of atrioventricular (AV) blocks.

BACKGROUND OF THE INVENTION

The normal cardiac cycle includes contractions of the atrial muscles, which are activated by the autonomic sinoatrial node (SA node), also called the sinus node. The electrophysiologic (EP) signal generated by the SA node spreads in the right and left atrium leading to their contraction. The EP signal further reaches the atrioventricular node (AV node) situated between the atria and the ventricles. The AV node delays the EP signal, giving the atria time to contract completely before the ventricles are stimulated. After the delay in the AV node the EP signal spreads to the ventricles via the fibers of the His-Purkinje system leading to the contraction of the ventricles. After the contraction the atria are relaxed and filled by blood coming from venous return. The entire cardiac cycle is the combination of atrial and ventricular contraction, i.e. depolarization, and their relaxation, i.e. repolarization.

As is known, the cardiac cycle can be measured non-invasively by attaching small electrodes on the skin of the patient. The voltage differences caused by the heart between the electrodes are measured and recorded in order to obtain the electrocardiogram (ECG) of the patient.

In this connection, reference is made to FIG. 1, which shows one cycle of an ECG signal. As is commonly known, and also shown in the figure, the waves of the ECG signal (i.e. the depolarisation and repolarisation events in the heart) are named alphabetically from P to U. The ECG signal shows each phase of the cardiac cycle: the P wave represents the systole of the atria, the QRS wave represents the systole of ventricles, and T wave represents the repolarization of the ventricles. Modern ECG devices use digital signal processing to analyze the shape and the consistency of, and the durations between these waveforms.

The heart rate (HR) can be measured by calculating the number of QRS waves in a minute. The HR may be expressed as a minute rate or as beats per minute (bpm). The rate of a heart functioning in a normal manner is not a constant, and the variation of the rate, which is commonly called the heart rate variability (HRV), has become one of the widely used markers for indicating the cardiac condition of a patient.

The ECG signal is thus analyzed for detecting various heart disorders, such as abnormalities in the heart rhythm, also termed arrhythmias. One of type of arrhythmia is an AV block, also termed a heart block, in which the signal flow from the atria to the ventricles is impaired. The AV blocks are classified into three different categories according to the level of impairment. In a first-degree AV block, the electrical impulse travels through the AV node more slowly than normal. If the PR interval measured from the ECG signal is more than about 0.2 seconds but less than about 0.6 seconds, it is regarded as the first-degree AV block. Normally, the first-degree AV block does not need treatment, but requires careful monitoring since it may progress to a more serious type of AV block. However, a difficulty in documenting a first-degree AV block is that such blocks are sporadic and may therefore not appear during a clinical visit. Instead, they may appear during the night time at home. In a second-degree AV block, some impulses from the atria do not reach the ventricles. In this case, the relevant P wave is not followed by a QRS complex, since the ventricles are not activated. FIG. 2 shows an ECG signal in which P wave P(n), i.e. the P wave of the cardiac cycle with index n, is not followed by a QRS complex. There are two types of second-degree AV blocks; type I and type II. Both types may progress to a third-degree AV block. However, as type II second-degree block may do that rapidly, it is more serious than type I. In a third-degree AV block, the electrical impulses from the atria do not reach the ventricles, i.e. there is a total block of atrial impulses to the ventricles. The third-degree AV block involves a serious risk of sudden cardiac death and therefore requires a pacemaker to be implanted immediately. A temporary pacemaker may also be used until a surgery can be performed.

At present, the detection of AV blocks is commonly based on the ECG interpretation performed by physicians. As this cannot normally be carried out in real-time, it is difficult to get a real-time indication of the onset of an AV block or of a rapid progress of the AV block. Furthermore, documentation of sporadically occurring AV blocks is difficult, since it requires ECG signal data to be collected over a long time period.

A further difficulty related to the monitoring of atrial activity is that Bundle Branch Blocks (BBBs), for example, may suddenly cause a substantial drop in the amplitude of the QRS complexes. The detection of these low amplitude QRS complexes may be complicated, since the improved detection sensitivity required by the lower amplitudes tends to translate to an increased number of erroneous detections caused by artifacts, for example.

The present invention seeks to provide a mechanism for eliminating or alleviating the above drawbacks related to the monitoring of atrial activation.

SUMMARY OF THE INVENTION

The present invention seeks to bring about a new solution for monitoring atrial activation, which allows efficient detection of QRS complexes and automatic and reliable detection of atrioventricular (AV) blocks in real-time. The invention further seeks to accomplish a solution that allows detection of rarely occurring AV blocks in non-clinical environments.

In the present invention, previous P waves detected from the ECG signal of a patient are used to predict the wave form and the moment of occurrence of the next P wave in the ECG signal. The actual ECG signal at and around the predicted moment is then examined to verify, if the ECG signal really contained a P wave at, or substantially at, the predicted moment. If this is the case, the system jumps to a monitoring step to monitor whether the P wave is followed by a QRS complex. The monitoring step may be performed in various ways depending on the application in question. When AV blocks are monitored, a timer, here termed an AV block timer, is started to measure a time window during which the next QRS complex is monitored. If the next QRS complex is not detected before the AV block timer expires, i.e. before the time window closes, an AV block is detected. However, an AV block may also be detected if the occurrence of the next QRS complex is delayed. In a further embodiment of the invention, the wave form and the moment of occurrence of the next QRS complex are predicted in the monitoring step. In this way, a fast QRS detection process may be provided. In a still further embodiment of the invention, the monitoring step is controlled by supplying an indication informing the QRS detection process to use a lower detection threshold temporarily, the indication being supplied in response to a verified P wave. In this way, the detection of low amplitude QRS complexes may be improved.

Thus one aspect of the invention is providing a method for monitoring atrial activation in an individual patient. The method includes receiving ECG signal data, predicting, based on a first sequence of P waves received in the ECG signal data, a moment of occurrence for a subsequent P wave in the ECG signal data, and estimating a reference wave form for the subsequent P wave based on a second sequence of P waves received in the ECG signal data. The method further includes the steps of checking whether said subsequent P wave occurs in the ECG signal data within a first time window around the moment of occurrence and monitoring whether a subsequent QRS complex occurs in the ECG signal data after said subsequent P wave, wherein the monitoring step is performed upon detecting in the checking step that said subsequent P wave occurred in the ECG signal data within the first time window.

The invention provides a mechanism that reliably detects AV blocks and allows the clinical and nursing staff to be informed of the occurrence and recurrence of AV blocks. A further advantage of the invention is that AV blocks may be detected in real-time, which allows an alarm of the onset to be given quickly.

Another aspect of the invention is that of providing a system for monitoring atrial activation in an individual patient. The system includes reception means for receiving ECG signal data and first calculation means for predicting a moment of occurrence for a subsequent P wave in the ECG signal data, the first calculation means being configured to predict the moment of occurrence based on a first sequence of P waves received in the ECG signal data. The system further includes second calculation means for estimating a reference wave form for the subsequent P wave based on a second sequence of P waves received in the ECG signal data, first verification means for checking whether said subsequent P wave occurs in the ECG signal data within a first time window around the moment of occurrence, and monitoring means for monitoring whether a subsequent QRS complex occurs in the ECG signal data after said subsequent P wave.

A still further aspect of the invention is that of providing a computer program product by means of which known ECG devices may be upgraded to enable automatic detection of AV blocks. The program product includes a first program code portion configured to predict, based on a first sequence of P waves contained in ECG signal data obtained from a patient, a moment of occurrence for a subsequent P wave in the ECG signal data, a second program code portion configured to estimate a reference wave form for the subsequent P wave based on a second sequence of P waves received in the ECG signal data, a third program code portion configured to check whether said subsequent P wave occurs in the ECG signal data within a first time window around the moment of occurrence, and a fourth program code portion configured to monitor whether a subsequent QRS complex occurs in the ECG signal data after said subsequent P wave.

Other features and advantages of the invention will become apparent by reference to the following detailed description and accompanying drawings.

BRIEF DESCRIPTION OF THE DRAWINGS

In the following, the invention and many of its embodiments are described more closely with reference to the examples shown in FIGS. 3 to 10 in the appended drawings, wherein:

FIG. 4a illustrates the performance of different prediction methods for predicting the moment of an upcoming P wave;

FIG. 5 illustrates the performance of a prediction method based on a second order polynomial, when used with and without a correction step for correcting the predicted estimate;

FIG. 6 shows an example of the improvement of the prediction result when using the correction step;

DETAILED DESCRIPTION OF THE INVENTION

As discussed above, during a normal sinus rhythm the P waves are conducted to the ventricles, i.e. each P wave P(i) is followed by a QRS complex R(i). Therefore, a P wave can normally be detected by first detecting the subsequent QRS. However, since in the case of an AV block a P wave may not be followed by a QRS complex, the relevant P wave cannot be detected based on QRS detection. In the following, the said relevant P wave is denoted P(n). Therefore, in order to detect an AV block, the relevant P wave needs to be detected independently of the detection of the QRS complex in the same cardiac cycle.

In the present invention, the above facts are utilized by storing information about the P waves detected during normal sinus rhythm. This information is used to predict the moment of occurrence and the morphology of the relevant P wave P(n). Here, morphology refers to the shape and magnitude of the P wave. Since information about a certain number K of previous P waves (P(n−1), P(n−2), ..., P(n−K)) is available at each time, the said information may be utilized to predict the moment and morphology of the next P wave P(n). Furthermore, since the variability of the PP interval is normally low and since the morphology of the P waves remains stable, the moment and morphology of the next P wave may be predicted accurately. The PP interval here refers to the interval between successive P waves.

Figure 1:
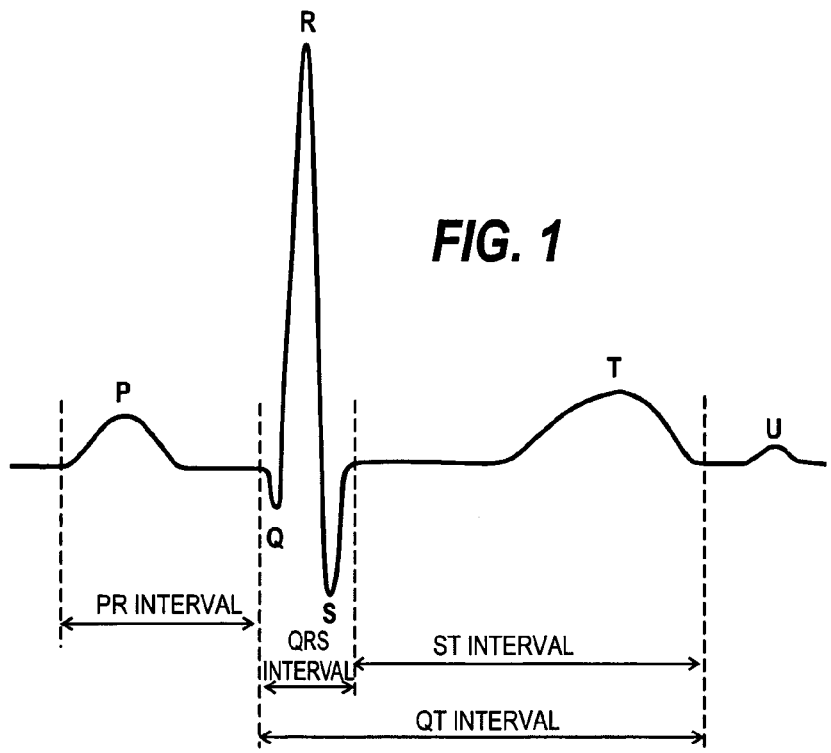
FIG. 1 illustrates an ECG signal of one cardiac cycle.
Figure 2:
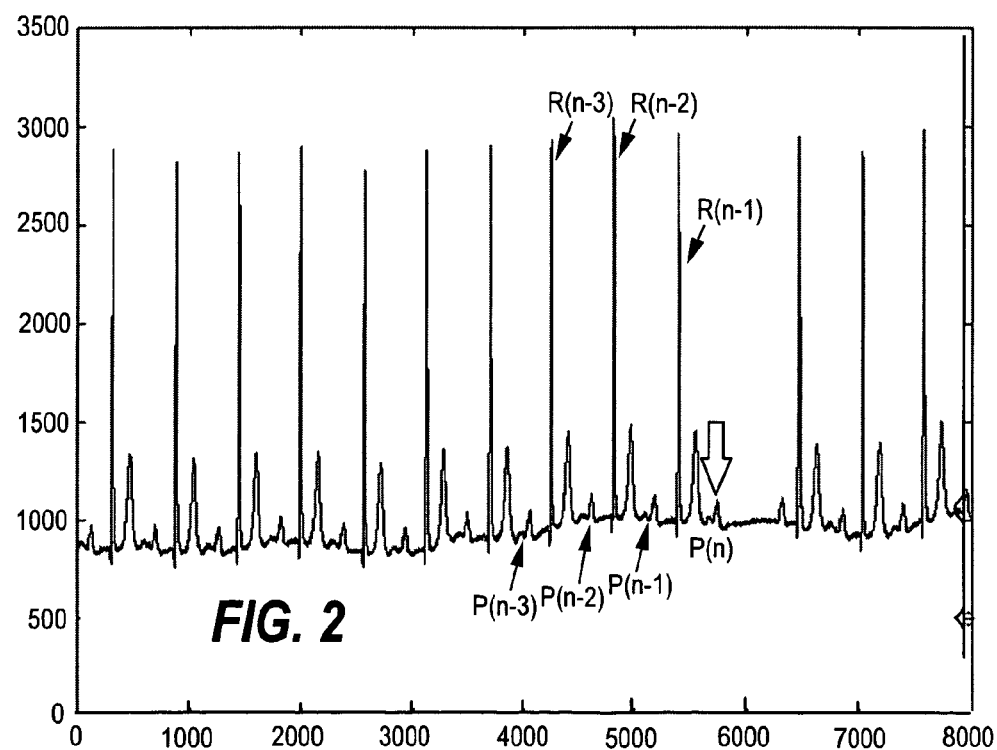
FIG. 2 shows an ECG signal sequence in which an AV block is visible.
Figure 3:
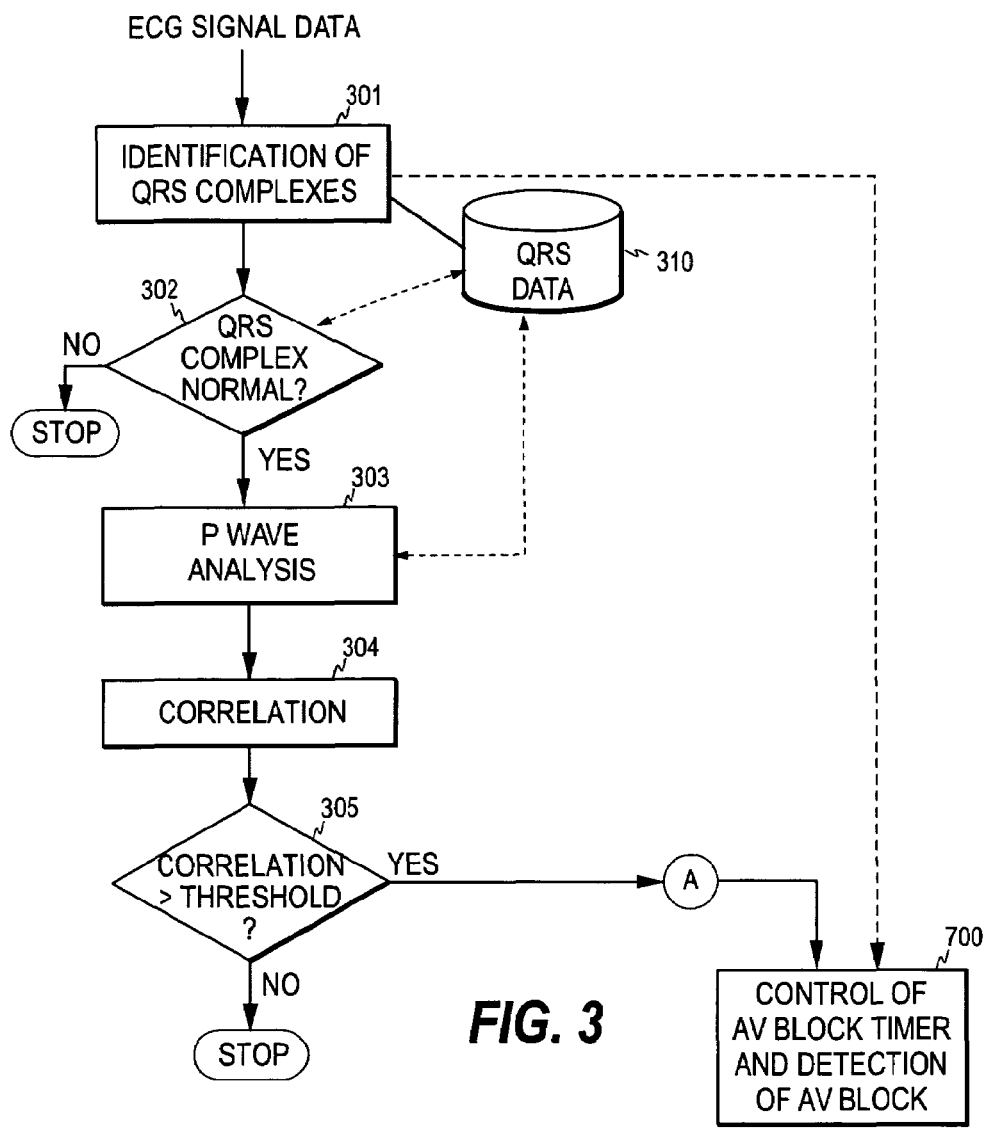
FIG. 3 is a flow diagram illustrating one embodiment of the invention.

FIG. 3 illustrates one embodiment of the invention. As mentioned above, the present invention utilizes existing methods for identifying QRS complexes. Therefore, the ECG signal data obtained from a patient is first supplied to a QRS detection process (step 301), in which the QRS complexes are identified using known detection methods. The QRS detection process is thus a process that detects the QRS waves from the ECG signal and provides the ECG signal data with the metadata necessary for the utilization of the signal data. This metadata may include, for example, data indicating whether the QRS complex is normal or not. QRS detection processes are disclosed for example in the article "The principles of software QRS detection", Kohler, B.-U.; Hennig, C.; Orglmeister, R.; Engineering in Medicine and Biology Magazine, IEEE, January-February 2002, Vol. 21, Issue 1, pp. 42-57.

The QRS detection process further includes the detection of the P waves. The detection may be implemented, for example, by finding a maximum or minimum, i.e. the P wave spike, between the onset of the current QRS complex and the end point of the previous T wave. Since in the case of an AV block the PQ time may be more than 200 ms, the detection window must extend more than 200 ms backwards from the onset of the current QRS complex. The P wave may be stored, for example, as a vector of the ECG samples around the P wave spike. The total length of the vector may be, for example, 100 ms.

The QRS detection process thus typically stores data that indicates the moments and morphologies of both the ORS complexes and the corresponding P waves. The said data, together with the associated metadata, is here termed QRS data. As discussed below, the QRS data concerning the P waves is utilized in the present invention to detect AV blocks.

Based on the QRS data obtained, it is first tested, whether the QRS complex is normal (step 302). If the metadata of the QRS detection process provides the said information, it may be retrieved directly from the memory 310 holding the QRS data. However, if this is not the case, the normality of the QRS complex may be evaluated at step 302 by means of a known arrhythmia algorithm.

If the QRS complex is normal, a P wave analysis is performed at step 303. In the P wave analysis, the moment of occurrence of the subsequent P wave is predicted after each PP interval. The P wave analysis also yields an estimate of the P wave morphology, which is here termed a reference P wave. The P wave analysis is discussed in more detail below, after the general procedure of the embodiment of FIG. 3 has been examined.

The P wave analysis thus provides the predicted moment of occurrence for the next P wave P(n), i.e. the P wave in the next cardiac cycle, and the reference P wave, which is an estimate of the wave form of the said next P wave.

The process then verifies at steps 304 and 305, if a P wave really occurred in the ECG signal substantially at the predicted moment of occurrence. For this purpose, a local maximum/minimum is first searched for in a predefined time window including the predicted moment of occurrence. The time window, which is here termed the first time window, may extend, for example, 50 ms to both directions from the predicted moment of occurrence. A local extremum found in the first time window is then assumed to represent the peak of the predicted P wave. The correlation between the reference P wave and an ECG signal data segment around the local maximum/minimum is then calculated at step 304. The length of the data segment corresponds to that of the reference P wave. The correlation process thus examines how well the actual signal data around a local maximum/minimum occurring substantially at the predicted moment of occurrence matches the reference P wave. In order to test whether the predicted P wave has a high correlation with the reference P wave, any variable or combination of variables indicative of the degree of correlation may be utilized. For example, simple template matching may be applied by calculating the differences of the corresponding data points of the two waves and summing the absolute values of the differences. Another example of a variable suitable for this purpose is the ratio of the maximum difference between the two waves to the amplitude of the reference P wave.

If it is detected at step 305 that the correlation is greater than a predefined threshold, the process decides that a P wave occurred at the predicted moment of occurrence in the ECG signal. For example, if the absolute value of the sum is below a given threshold, such as one eighth of the amplitude of the reference P wave, the process decides that the correlation is high enough. The process then jumps to step 700, in which an AV block is monitored by controlling a timer, which is here termed the AV block timer.

If the correlation is lower than the threshold, it is decided that no P wave is detected and the process ends for the current P wave. The next P wave is estimated similarly.

In the P wave analysis (step 303), the moment of the next P wave is estimated by first calculating a weighted sum of the previous K+1 PP intervals PP(t−i) as follows:

$$PP(t+1) = \sum_i A(t-i) \times PP(t-i), \quad (1)$$

where i=0 ... K is the index of previous PP intervals before current time t.

The simplest method to define the weights A(t−i) would be to set them to 1/(K+1). Thus, in this case the average of previous PP intervals is calculated:

$$PP(t+1) = \sum_i \frac{1}{K+1} \times PP(t-i),$$

where the index i goes from 0 to K.

However, determining the average of a predetermined number of previous PP intervals is not the best method to predict the moment of the next P wave, since the PP interval does not change linearly when the heart rate changes. This is illustrated in FIG. 4a, where the continuous line shows the PP intervals measured during a rhythm change. In this case, the heart rate is decreasing and the values of the PP intervals thus increase during the change of the sinus rhythm. FIG. 4a further illustrates the prediction results obtained by four different type of prediction models, which are based on first, second, and third order polynomials, and on the above-mentioned average. In this example, K equals 14. As can be seen from the figure, the second and third order polynomial prediction models adapt quickly during the change of the rhythm. Maximum prediction error (ME(t−i)) is in this example 5.3% for the second order polynomial and 17.4% for the average. This means that using the simple average-based prediction method during the change of the heart rate the accuracy obtained is not as good as when using a prediction model based on a second order polynomial. Furthermore, polynomials of higher orders do not significantly improve the accuracy of the predicted PP interval. Therefore, a second order polynomial is the preferred model for modelling the behaviour of the PP intervals in connection with the prediction of the moment of the next P wave.

In one embodiment of the invention, the previous PP intervals are utilized by deriving three consecutive moving averages from 3L previous PP intervals, where L is a predetermined integer. The equation for estimating the length of the next PP interval $PP\_pred(t+1)$ may then be depicted as follows:

$$PP\_pred(t+1)=(A1*AVE\_L(t)+A2*AVE\_L(t-L)+ A3*AVE\_L(t-2L))/(A1+A2+A3), \quad (2)$$

where AVE_L(t) is a moving average of L previous PP intervals at time t. In this example L=5, i.e. 15 previous PP intervals are utilized.

Figure 4B:
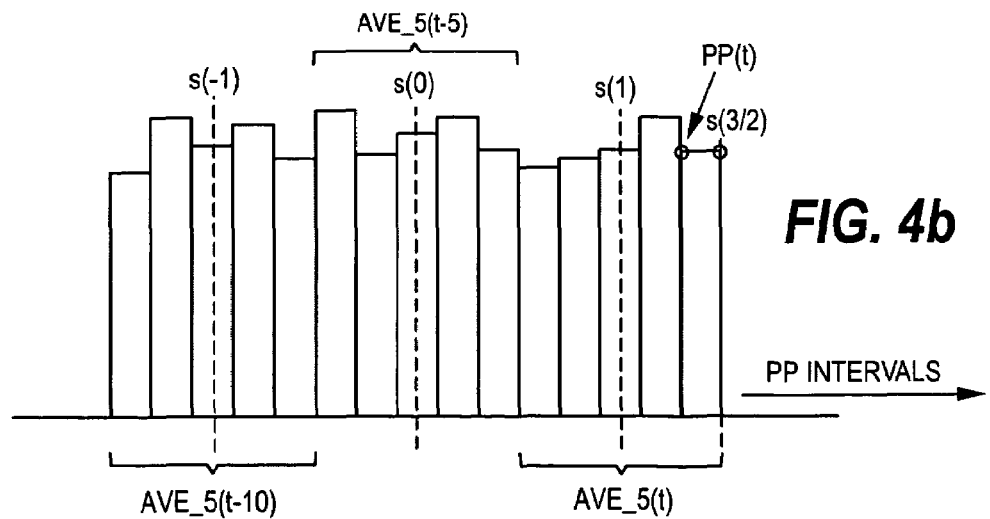
FIG. 4b is a time line illustrating the use of PP intervals for predicting the moment of occurrence for a subsequent P wave.

The above equation may be adapted to a second order polynomial by defining the coefficients A1, A2, and A3 using a second order polynomial $s(t)=a \times t^2+b \times t+c$. This may be carried out by setting s(1)=AVE5(t), s(0)=AVE5(t−5) and s(−1)=AVE5(t−10), and solving s(t=3/2). In this case, s(t=3/2) is the prediction point, as is illustrated in the time line of FIG. 4b showing consecutive PP intervals. Each PP interval PP(t−i) is the current interval from t=(t−i) until t=(t−i+1). Therefore, since the middle points of the moving averages AVE5(t−10), AVE5(t−5), and AVE5(t) correspond to s(−1), s(0), and s(1), respectively, the predicted moment corresponds to s(3/2). When t=3/2 is regarded as the prediction point, coefficient values A1=3, A2=−10, and A3=15 are obtained.

If a third order polynomial is utilized in the prediction, the equation for $PP_{pred}(t+1)$ becomes:

$$PP_{pred}(t+1)=(A1*AVE\_L(t)+A2*AVE\_L(t-L)+A3*AVE\_L(t-2L)+A4*AVE\_L(t-3L))/(A1+A2+A3+A4) \quad (3)$$

where $AVE\_L(t)$ is the moving average of L previous PP intervals at time t.

The coefficients may be solved as described above by utilizing a third order polynomial.

After the next PP interval $PP_{pred}(t+1)$ has been calculated, the moment of the next P wave $T_{P(t+1)}$ may be derived according to equation (4) by adding the estimated PP interval value to the moment of the current P wave $T_{P(t)}$:

$$T_{P(t+1)}=T_{P(t)}+PP_{pred}(t+1) \quad (4)$$

The obtained estimates may further be corrected by using a prediction error estimate $E_{est}(t+1)$ defined as follows:

$$E_{est}(t+1)=PP(t)-PP_{pred}(t) \quad (5)$$

The error measured in connection with the previous prediction may thus be used as the prediction error. A corrected estimate for the length of the next PP interval $PP_{pred}(t+1)$ is then obtained as follows:

$$PP_{corrected}(t+1)=PP_{pred}(t+1)+E_{est}(t+1) \quad (6)$$

FIGS. 5 and 6 illustrate how the use of the corrected estimate decreases the error in the predicted PP interval. FIG. 5 shows the measured PP intervals, the estimated PP intervals, and the estimated PP intervals, which are further corrected as discussed above. FIG. 6 shows the error of the estimate and the corrected estimate. In the above example, the maximum error decreased from 5.3% to 2.8% when the corrected estimate was taken into use. The accuracy of the prediction may be evaluated by comparing the P wave detections made by the QRS detection process to the estimations calculated and by calculating the Mean Square Error (MSE) for the predicted moments. The MSE approaches zero if the predicted moments accurately represent the true moments of the P waves. Therefore, the MSE is measure of the quality of the estimation model. It defines a window around the estimated moment of the P wave, where the P wave should be.

As mentioned above, P wave analysis further outputs the reference P wave, which is an estimate of the wave form of the P wave whose moment of occurrence is predicted. The current reference P wave ref_P_wave(t) may be calculated as an incremental average as follows:

$$ref\_P\_wave(t)=((N-1)\times ref\_P\_wave(t-1)+P\_wave(t))/N,$$

where P_wave(t) is the current P wave, ref_P_wave(t−1) is the previous reference P wave calculated, and N is a predefined integer, whose value is typically between 4 and 8. When calculating the reference P wave, the average may be calculated for each data point of the P wave vector.

Alternatively, the current reference P wave ref_P_wave(t) may be calculated as a normal average based on N previous P wave forms:

$$ref\_P\_wave(t) = \sum_{i=0}^{i=(N-1)} (P\_wave(t-i))/N.$$

Figure 7:
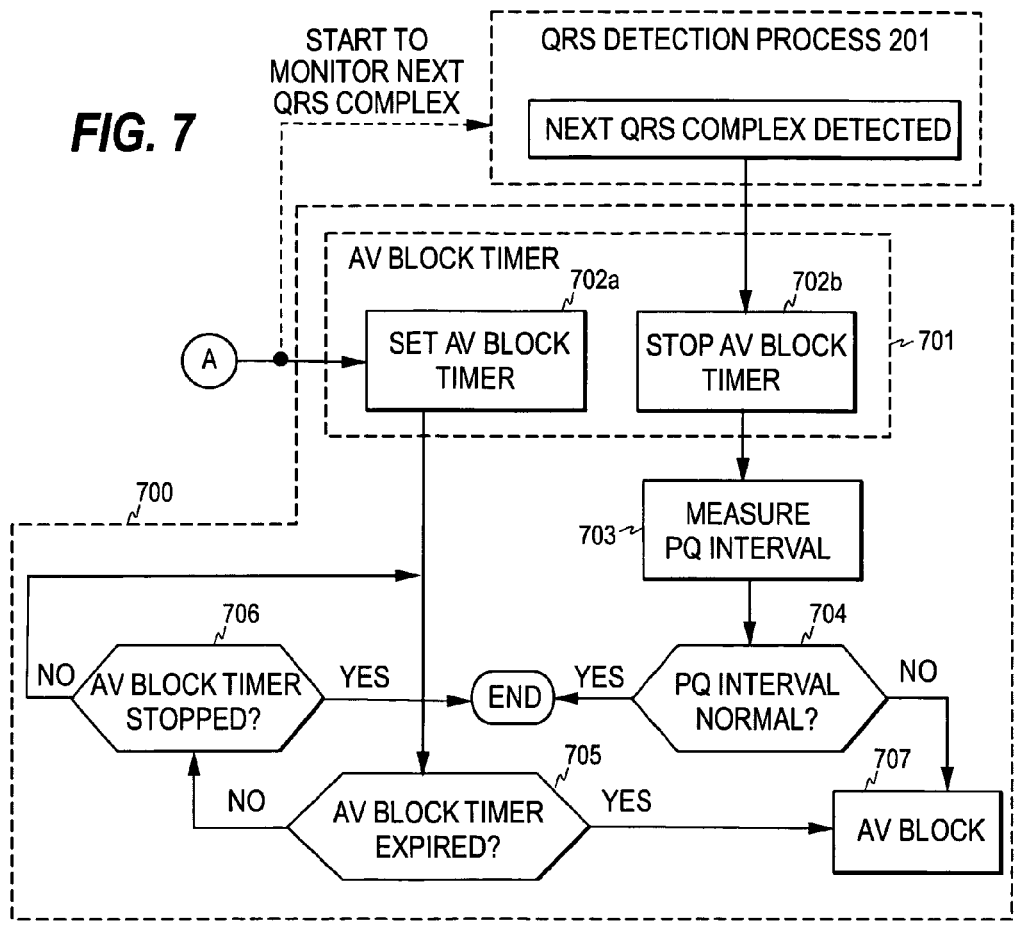
FIG. 7 illustrates the control of the AV block timer and the detection of the AV block in the embodiment of FIG. 3.

FIG. 7 illustrates one embodiment of the control the AV block timer and the detection of the AV blocks. As mentioned above in connection with FIG. 3, the process jumps to step 700 if it is detected that the ECG signal contained a P wave substantially at the predicted moment of occurrence. When this occurs, the AV block timer 701 is set to expire after a predetermined measuring period at step 702a. Simultaneously, the QRS detection process 201 starts to monitor the occurrence of the subsequent QRS complex. The AV block timer is thus set to measure a time window within which the occurrence of the subsequent QRS complex is monitored. This time window is here termed the second time window to distinguish it from the first time window used for finding the predicted P wave. As is obvious from the above, the second time window may start substantially from the local extremum found in the first time window. Generally, however, the second time window may start before or after the first time window closes.

If the next QRS complex is detected within the second time window, i.e. before the timer expires, the QRS detection process stops the AV block timer (step 702b). In response to this, the latest PQ interval is measured at step 704. If the PQ interval is normal, i.e. shorter than about 0.2 seconds, no AV block is detected and the process ends. However, if the PQ interval is longer than normally, an AV block is detected (step 707). In this case an AV block of first-degree is in question.

An AV block is also detected if the QRS detection process is not able to detect a QRS complex before the AV block timer expires (steps 705 and 707). In this case, a second-degree or a third-degree AV block may be in question. In case of regular RR intervals a third-degree AV block is considered if PP intervals indicate a faster rhythm than RR intervals. In this case the PQ intervals are normally irregular, since in case of a third-degree AV block the atrial and ventricular rhythms originate from different sources. In case of irregular RR intervals a second-degree AV block is detected. In this case, the type of the second-degree AV block is determined by PQ intervals. In case of regular PQ intervals, type II second-degree AV block is considered, while in case of irregular PQ intervals type I second-degree AV block is considered.

In the above embodiments, the QRS detection process further takes care that the P wave data is updated. Each time the QRS detection process detects a QRS complex, it replaces the oldest P wave in the memory by the data of the P wave preceding the newly detected QRS complex.

Instead of AV block detection, the mechanism of the invention may also be utilized for other applications related to the monitoring of atrial activity. This is discussed in the following.

Figure 8:
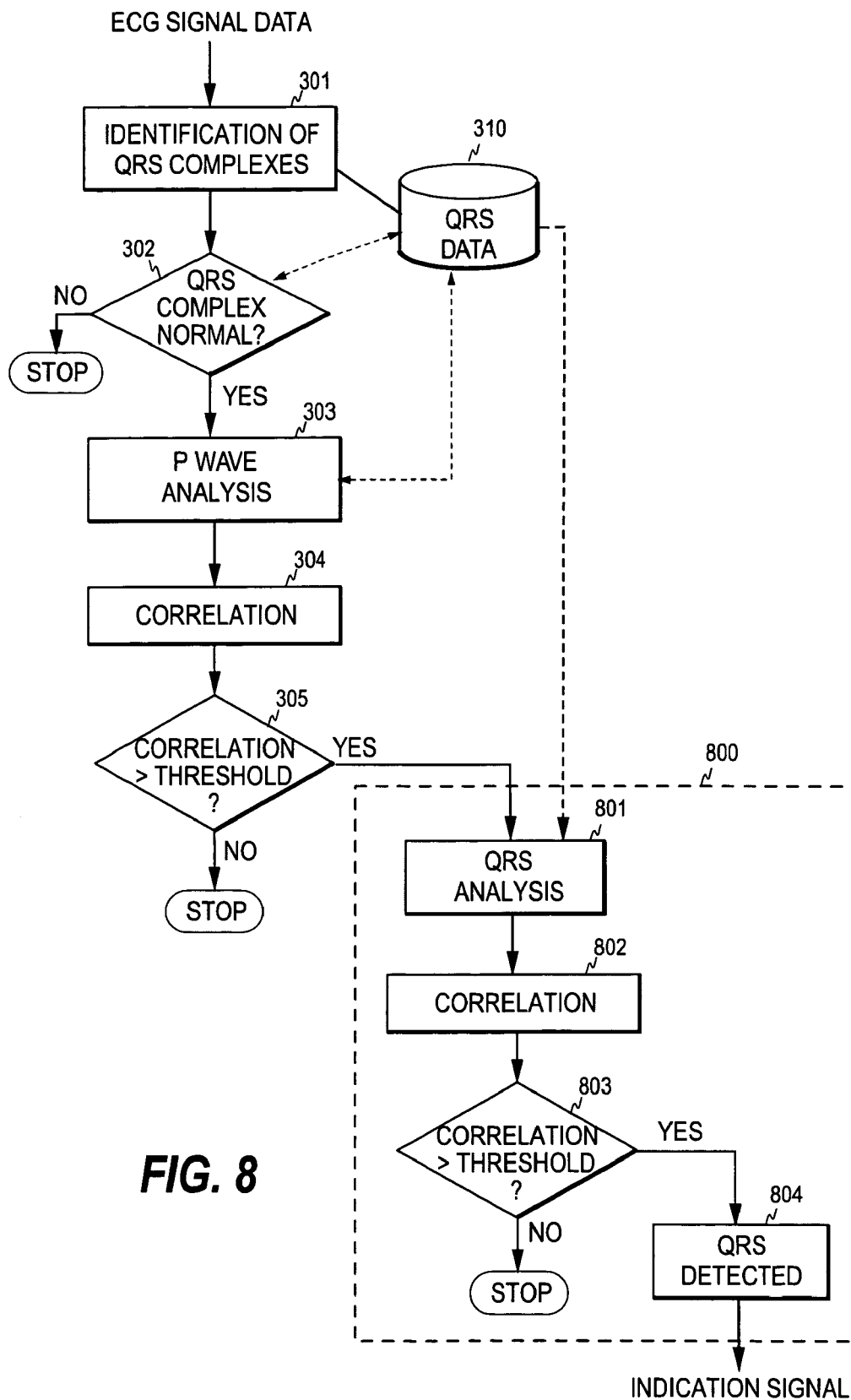
FIG. 8 illustrates an embodiment of the invention used for fast QRS detection.

In one embodiment of the invention, which is illustrated in FIG. 8, the mechanism may be utilized to provide a fast QRS detection. This embodiment is similar to the embodiment of FIG. 3, except that no timer is started after step 305, if it is detected that the P wave really occurred at the predicted moment of occurrence. Instead, the process jumps to a predictive QRS analysis stage 800, in which an analysis similar to the one performed earlier at steps 303 to 305 for the next P wave is now performed for the next QRS complex. In the predictive QRS analysis, the moment of occurrence and the wave form of the next QRS complex are first predicted at step 801. The determination of the moment of occurrence of the next QRS complex may be based on an average PQ interval, for example, while the determination of the reference QRS complex may be performed similarly as the determination of the reference P wave in step 303. Next, the correlation between the reference QRS complex and an ECG signal data segment selected based on the predicted moment of occurrence of the QRS complex is calculated at step 802. If it is then detected at step 803 that this correlation exceeds a predefined threshold, the process decides that a QRS complex really occurred in the ECG signal data substantially at the predicted moment of occurrence (step 804).

In this embodiment, the QRS detection process is thus divided into a conventional part, which includes the QRS data collected based on previous QRS complexes, and a predictive part (303 to 305 and 800), in which the moment of occurrence and the wave form of the next P wave are first predicted. Then, if the predicted P wave is detected, the moment of occurrence and the wave form of the next QRS complex are further predicted and ECG signal data around the predicted moment of occurrence is examined to see whether a QRS complex occurred substantially at the predicted moment of occurrence.

Using the above-described detection mechanism, the next QRS complex may be detected with a delay of about 20 ms only, which is less than the delay of most conventional QRS detection processes. This allows the detection process to be used in connection with applications requiring fast QRS detection. Such applications may include, for example, ECG monitoring in connection with the use of Magnetic Resonance Imaging (MRI) devices, defibrillators, or Intra Aortic Balloon Pumps (IABPs).

Figure 9:
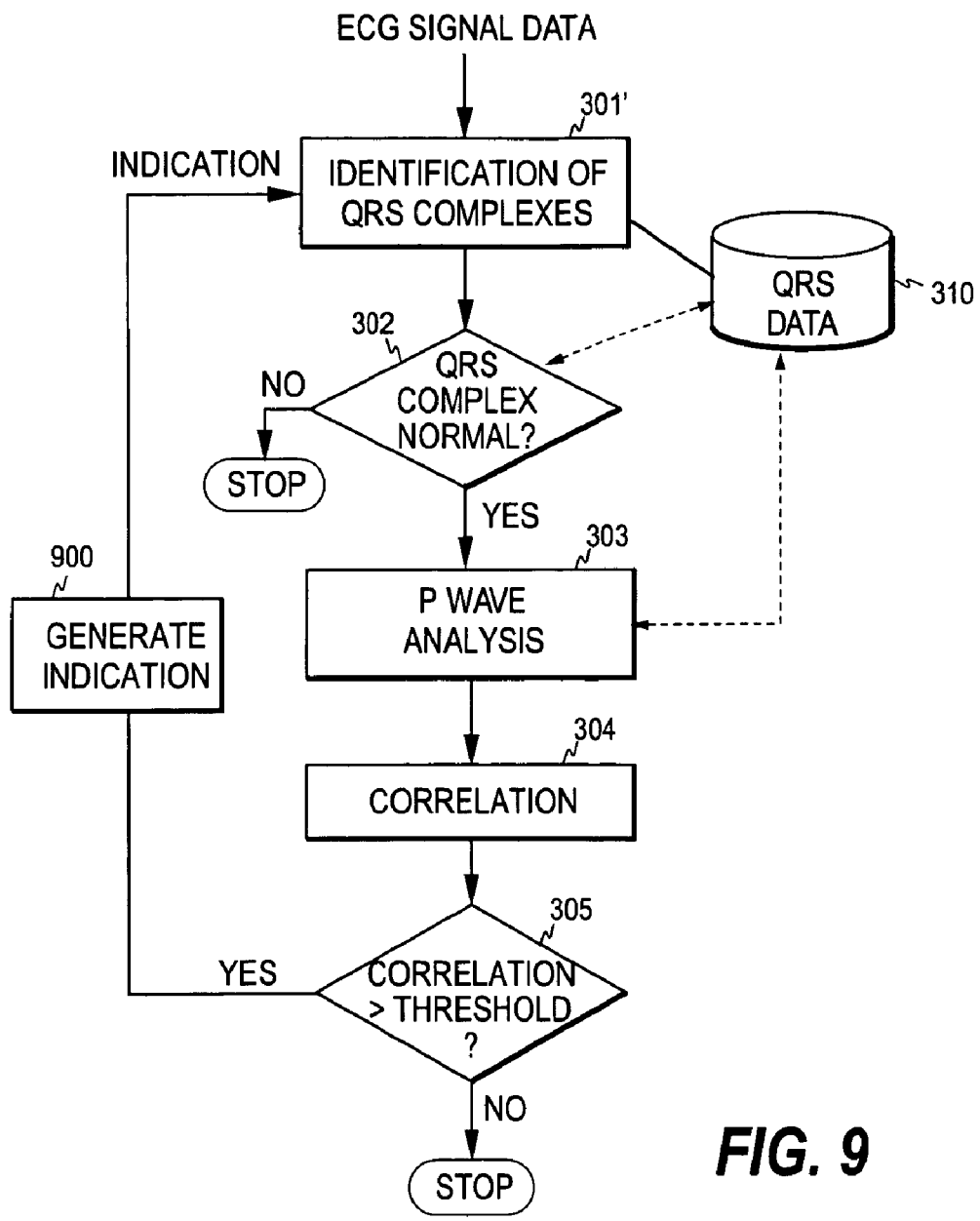
FIG. 9 illustrates an embodiment of the invention used for detecting low amplitude QRS complexes.

One difficulty related to the QRS detection is that the amplitude of the QRS complex may suddenly drop due to a Bundle Branch Block (BBB), for example, which may make it difficult for the QRS detection process to detect the QRS complexes. Normally, the QRS complex is detected if the ECG wave reaches a predefined threshold level, which must be high enough to avoid erroneous detections caused by artifacts, for example. However, due to a Bundle Branch Block (BBB), for example, the peak amplitude of the QRS complex may drop even below the said threshold level. In these cases, false arrhythmia call, such as asystole, may occur. However, in one embodiment of the invention, which is illustrated in FIG. 9, the above-described mechanism may be utilized to provide detection of low amplitude QRS complexes. In this embodiment, an indication is given (step 900) to the QRS detection process when the predicted P wave has been verified at step 305. In response to the indication, the above-mentioned threshold may be lowered in a short time window within which the next QRS complex will most likely occur. In this way, the ability of the QRS detection process to detect low amplitude QRS complexes may be improved without causing false detections. In this embodiment, the QRS detection process 301' is thus provided with a controller for changing the threshold level in response to the indication.

Figure 10:
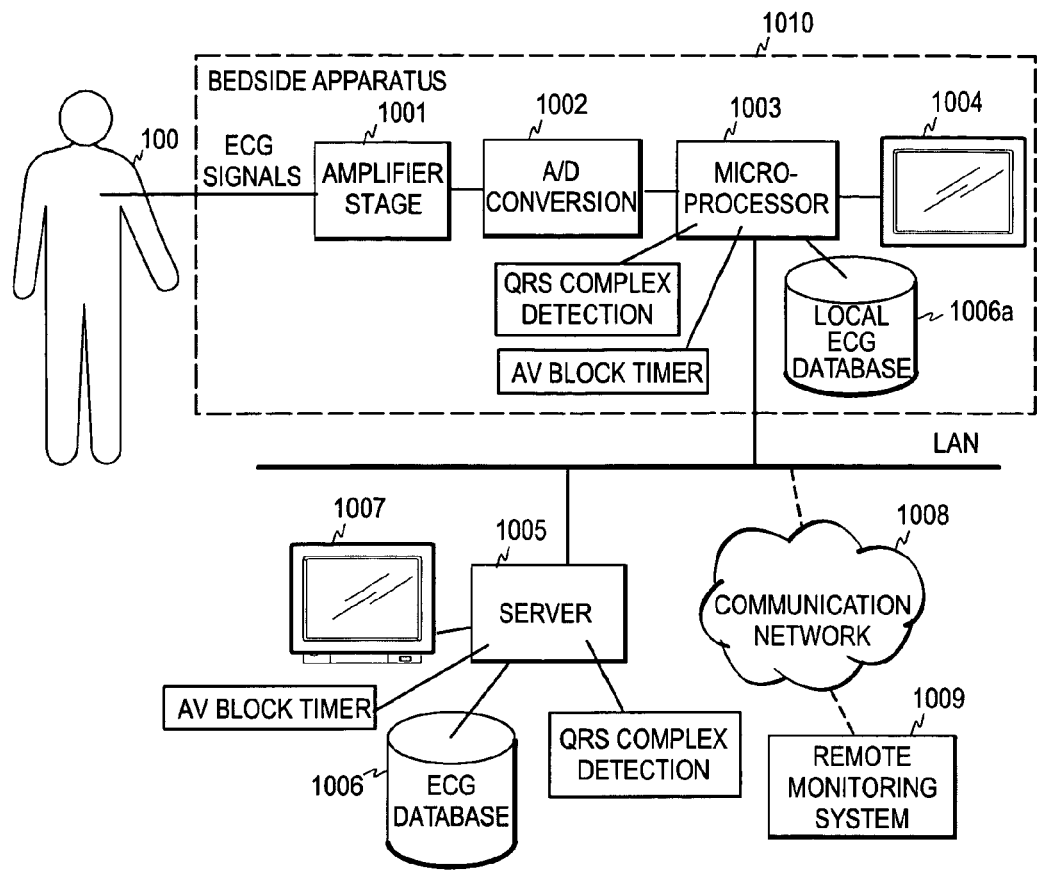
FIG. 10 illustrates one embodiment of the system of the invention in a hospital environment.

FIG. 10 illustrates one embodiment of the system according to the invention. The ECG signals obtained from the different sensors attached to a patient 100 are supplied to an amplifier stage 1001, which amplifies the signals before they are sampled and converted into digitized format in an A/D converter 1002. The digitized signals are supplied to a microprocessor 1003 which may then carry out artifact rejection, for example. The digitized ECG signal data is then supplied to the QRS detection process residing either in the microprocessor or in a centralized server 1005, depending on whether atrial activity is monitored locally in a bedside monitor 1010 or in a centralized manner in a server 1005 of the hospital local area network (LAN). The centralized server may serve one or more bedside monitors 1010.

The microprocessor may thus be connected to the local area network of the hospital for transferring the ECG signal data of a patient to a centralized server 1005. The server may be provided with a database 1006 holding the ECG signal data received from one or more bedside monitors 1010 and the QRS data derived from the ECG signal data. However, if atrial activity is monitored locally in the bedside monitor, the ECG signal data and the QRS data are stored in a local memory 1006a in connection with the bedside monitor.

The local microprocessor or the centralized server thus performs the above-described monitoring of atrial activity. A remote monitoring system 1009 may further be connected to the LAN through a communication network 1008 in order to monitor the results from a remote location. The remote monitoring system may also include one or more bedside monitors that send their ECG data to the centralized server for monitoring atrial activity, such as AV blocks, at a remote location. The microprocessor and/or the server may further be provided with a display unit 1004 respectively 1007 for displaying the ECG signal data and the results of the AV block detection.

The system of the invention may also be implemented as a compact measuring device, which may be used for long-term monitoring in non-clinical environments. In this case, the bedside monitor may be implemented as a portable measuring instrument, which the patient may use at home, for example, to document the occurrence of an AV block. In this case, the display unit is an integrated part of the housing of the measuring instrument.

The software enabling a conventional ECG measurement device to automatically detect an AV block may also be delivered separately to the measurement device, for example on a data carrier, such as a CD or a memory card. In other words, a conventional measurement device may be upgraded by a plug-in unit that includes software enabling the measurement device to detect an AV block based on the ECG signal data it has obtained from the patient. The plug-in unit is provided with an interface to the QRS detection process for utilization of the QRS data available in the ECG measurement device. Therefore, the functionality of the plug-in unit may vary depending on the type of the QRS data available in the ECG measurement device. For example, the plug-in unit may or may not include an algorithm for the evaluation of the normality of the QRS complex, depending on whether this information is available in the QRS data or not.

Although the invention was described above with reference to the examples shown in the appended drawings, it is obvious that the invention is not limited to these, but may be modified by those skilled in the art without departing from the scope and spirit of the invention. For example, the measurement devices by which the ECG data is obtained from the patient may include various types of known devices or measurement methods.

The invention claimed is:

1. A method for monitoring atrial activation in an individual patient, the method comprising the steps of:
   receiving ECG signal data obtained from a patient;
   based on a first sequence of P waves received in the EGG signal data, predicting a moment of occurrence for a subsequent P wave in the ECG signal data;

estimating a reference wave form for the subsequent P wave based on a second sequence of P waves received in the ECG signal data;

checking whether said subsequent P wave occurs in the ECG signal data within a first time window around the predicted moment of occurrence;

monitoring whether a subsequent QRS complex occurs in the ECG signal data within a second time window ending after the first time window; and indicating the detection of an AV block if the subsequent QRS complex fails to occur in the ECG data within the second time window, wherein the monitoring step is performed upon detecting in the checking step that said subsequent P wave occurred in the ECG signal data within the first time window.

2. A method according to claim 1, wherein the predicting step includes the steps of:

calculating an estimate for a subsequent PP interval;

defining the moment of occurrence for the subsequent P wave based on the estimate.

3. A method according to claim 2, wherein the calculating step includes a sub-step of calculating a first predetermined number of moving averages, each moving average representing a moving average of a second predetermined number of previous PP intervals calculated at a moment of time specific to the moving average concerned.

4. A method according to claim 3, wherein the calculating step further includes a sub-step of determining a weighted sum of the moving averages.

5. A method according to claim 4, further comprising a step of determining weight values for the weighted sum of the moving averages.

6. A method according to claim 5, wherein the calculating sub-step includes calculating three moving averages.

7. A method according to claim 6, wherein the determining step includes a sub-step of adapting the weight values to a second order polynomial.

8. A method according to claim 1, wherein the estimating step includes calculating an average wave form based on the second sequence of P waves, wherein the average wave form represents the reference wave form for the subsequent P wave.

9. A method according to claim 1, wherein the checking step includes the steps of:

extracting a signal data sequence from the ECG signal data, the signal data sequence representing a time interval having a length substantially equal to that of the reference wave form and including the moment of occurrence predicted in the predicting step and;

correlating the signal data sequence with the reference wave form, whereby a correlation coefficient indicative of the relationship of the signal data sequence and the reference wave form is obtained; and deciding, based on the correlation coefficient, whether the monitoring step is to be performed.

10. A method according to claim 9, wherein the extracting step includes a sub-step of searching for a local extremum in said first time window.

11. A method according to claim 1, wherein the first sequence of P waves equals the second sequence of P waves.

12. A method according to claim 1, further comprising a step of controlling the monitoring step, wherein the controlling step includes changing a threshold level used for detecting the subsequent QRS complex.

13. A method for monitoring atrial activation in an individual patient, the method comprising the steps of:

receiving ECG signal data obtained from a patient;

based on a first sequence of P waves received in the ECG signal data, predicting a moment of occurrence for a subsequent P wave in the ECG signal data;

estimating a reference wave form for the subsequent P wave based on a second sequence of P waves received in the ECG signal data;

checking whether said subsequent P wave occurs in the ECG signal data within a first time window around the predicted moment of occurrence; and monitoring whether a subsequent QRS complex occurs in the ECG signal data after said subsequent P wave, wherein the monitoring step further includes the sub-steps of:

setting a timer to measure a second time window ending after the first time window, the subsequent QRS complex being monitored within the second time window;

stopping the timer when the subsequent QRS complex occurs in the ECG signal data within the second time window;

measuring a time interval between the setting and stopping sub-steps; and based on the time interval, deciding whether an AV block occurred in the ECG signal data, wherein the monitoring step is performed upon detecting in the checking step that said subsequent P wave occurred in the ECG signal data within the first time window.

14. A method for monitoring atrial activation in an individual patient, the method comprising the steps of:

receiving ECG signal data obtained from a patient;

based on a first sequence of P waves received in the ECG signal data, predicting a moment of occurrence for a subsequent P wave in the ECG signal data;

estimating a reference wave form for the subsequent P wave based on a second sequence of P waves received in the ECG signal data;

checking whether said subsequent P wave occurs in the ECG signal data within a first time window around the predicted moment of occurrence; and monitoring whether a subsequent QRS complex occurs in the ECG signal data after said subsequent P wave, wherein the monitoring step further includes the sub-steps of:

predicting a moment of occurrence for the subsequent QRS complex;

estimating a reference wave form for the subsequent QRS complex; and checking whether the subsequent QRS complex occurs in the ECG signal data substantially at the moment of occurrence predicted in the predicting sub-step.

15. A system for monitoring atrial activation in an individual patient, the system comprising:

reception means for receiving ECG signal data obtained from a patient;

first calculation means for predicting a moment of occurrence for a subsequent P wave in the ECG signal data, the first calculation means being configured to predict the moment of occurrence based on a first sequence of P waves received in the ECG signal data;

second calculation means for estimating a reference wave form for the subsequent P wave based on a second sequence of P waves received in the ECG signal data;

first verification means for checking whether said subsequent P wave occurs in the ECG signal data within a first time window around the moment of occurrence; and monitoring means for monitoring whether a subsequent QRS complex occurs in the ECG signal data within a second time window ending after the first time window and after said subsequent P wave, wherein the monitoring means indicates the detection of an AV block if the subsequent QRS complex fails to occur in the ECG data within the second time window.

16. A system according to claim 15, wherein the first calculation means are configured to calculate an estimate for a subsequent PP interval.

17. A system according to claim 16, wherein the first calculation means are further configured to
calculate a first predetermined number of moving averages, each moving average representing a moving average of a second predetermined number of previous PP intervals calculated at a moment of time specific to the moving average concerned; and
determine the estimate for the subsequent PP interval as a weighted sum of the moving averages.

18. A system according to claim 15, wherein second calculation means are configured to calculate an average wave form based on the second sequence of P waves.

19. A system according to claim 15, wherein the first verification means are configured to determine a correlation coefficient between a selected signal data sequence in the ECG signal data and the reference wave form.

20. A system according to claim 15, wherein the monitoring means comprise a timer.

21. A system according to claim 15, wherein the monitoring means comprise:
third calculation means for predicting a moment of occurrence for the subsequent QRS complex;
fourth calculation means for estimating a reference wave form for the subsequent QRS complex; and
second verification means for checking whether the subsequent QRS complex occurs in the ECG signal data substantially at the moment of occurrence predicted by the third calculation means.

22. A system according to claim 15, wherein the first verification means are configured to generate an indication upon detecting that the P wave occurs in the first time window, the first verification means being further configured to supply the indication to the monitoring means.

23. A system for monitoring atrial activation in an individual patient, the system comprising:

a first controller for receiving ECG signal data obtained from a patient;
a first calculator configured to predict a moment of occurrence for a subsequent P wave in the ECG signal data, the first calculator being configured to predict the moment of occurrence based on a first sequence of P waves received in the ECG signal data;
a second calculator configured to estimate a reference wave form for the subsequent P wave based on a second sequence of P waves received in the ECG signal data;
a second controller configured to check whether said subsequent P wave occurs in the ECG signal data within a first time window around the moment of occurrence; and
a third controller configured to monitor whether a subsequent QRS complex occurs in the ECG signal data within a second time window ending after the first time window and after said subsequent P wave,
wherein the system indicates the detection of an AV block if the subsequent QRS complex fails to occur in the ECG data within the second time window.

24. A computer readable medium for monitoring atrial activation in an individual patient, the computer program product comprising:
a first program code portion configured to predict, based on a first sequence of P waves contained in ECG signal data obtained from a patient, a moment of occurrence for a subsequent P wave in the ECG signal data;
a second program code portion configured to estimate a reference wave form for the subsequent P wave based on a second sequence of P waves received in the ECG signal data;
a third program code portion configured to check whether said subsequent P wave occurs in the ECG signal data within a first time window around the moment of occurrence; and
a fourth program code portion configured to monitor whether a subsequent QRS complex occurs in the ECG signal data within a second time window ending after the first time window and after said subsequent P wave,
wherein the computer program product indicates the detection of an AV block if the subsequent QRS complex fails to occur in the ECG data within the second time window.

* * * * *